United States Patent [19]
Hilger

[11] Patent Number: 4,692,146
[45] Date of Patent: Sep. 8, 1987

[54] MULTIPLE VASCULAR ACCESS PORT

[75] Inventor: Gerald E. Hilger, Medina, N.Y.

[73] Assignee: Cormed, Inc., Murray Hill, N.J.

[21] Appl. No.: 791,124

[22] Filed: Oct. 24, 1985

[51] Int. Cl.[4] .......................................... A61M 31/00
[52] U.S. Cl. ..................................... 604/93; 604/173;
604/175; 604/891
[58] Field of Search .................. 604/9, 131, 174, 175,
604/173, 93, 891

[56] References Cited
U.S. PATENT DOCUMENTS

| 3,640,269 | 2/1972 | Delgado | 604/93 |
|---|---|---|---|
| 3,923,060 | 12/1975 | Ellinwood, Jr. | |
| 4,140,122 | 2/1979 | Kuhl et al. | |
| 4,146,029 | 3/1979 | Ellinwood, Jr. | |
| 4,160,454 | 7/1979 | Foux | 604/173 |
| 4,496,343 | 1/1985 | Prosl et al. | 604/86 |
| 4,557,722 | 12/1985 | Harris | 604/9 |
| 4,569,675 | 2/1986 | Prosl et al. | 604/175 |

FOREIGN PATENT DOCUMENTS 0134745  3/1985  European Pat. Off. ............ 604/175

Primary Examiner—C. Fred Rosenbaum
Assistant Examiner—Sherri E. Vinyard
Attorney, Agent, or Firm—Kane, Dalsimer, Kane, Sullivan and Kurucz

[57] ABSTRACT

A multiple lumen vascular access port including a base, first and second lumens in the base, first and second catheters in communication with the first and second lumens, respectively, a boss in contiguous relationship to the first lumen to permit its identification by feel, metal tubes in the catheters proximate the lumens to prevent leakable puncture of the catheters in the event of penetration of the catheters by a needle, and a tube leading to the second lumen being recessed within a metal portion of the first lumen to prevent access thereto by a needle which might puncture it. The vascular access port can contain more than two lumens.

17 Claims, 11 Drawing Figures

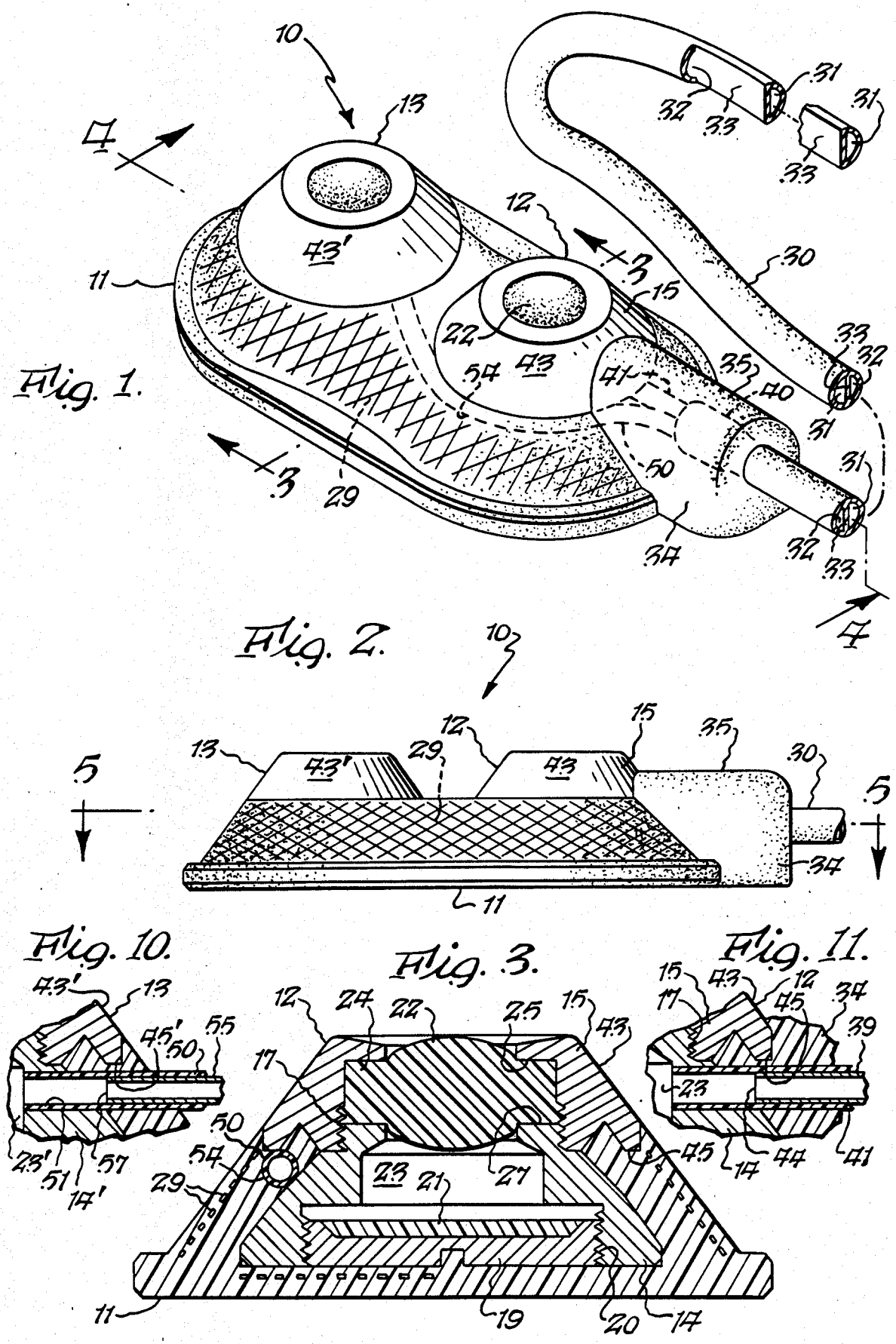

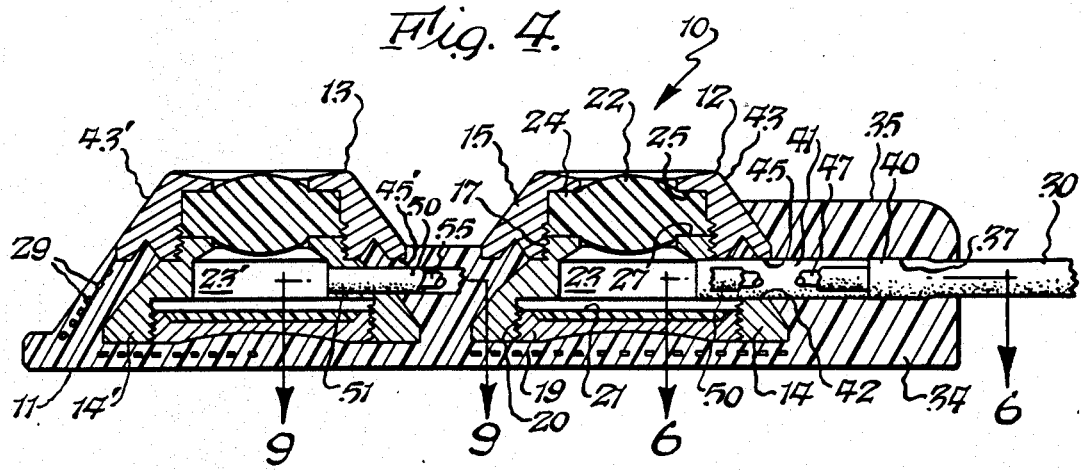

MULTIPLE VASCULAR ACCESS PORT

BACKGROUND OF THE INVENTION

The present invention relates to a multiple lumen implantable vascular access port.

By way of background, single lumen vascular access ports are presently known for receiving fluid from an infusion pump, syringe, or other source, and conducting it to an internal area of a patient's body through a catheter which is connected to the access port. The access port includes a chamber which receives fluid from a needle or cannula in communication with the external fluid source, and with the needle or cannula penetrating a septum of the access port.

In many patients, there is a requirement for infusion of more than one type of medication. If these medications are incompatible, a single implantable access port would not be adequate. In addition, many times there is a requirement to withdraw blood while simultaneously infusing medication. This obviously cannot be achieved with a single access port. Furthermore, the implanting of a plurality of access ports to achieve either of the foregoing is undesirable because each port has to be surgically implanted.

SUMMARY OF THE INVENTION

It is accordingly one object of the present invention to provide a multiple lumen implantable vascular access port which can be implanted in a single surgical procedure and which can distribute medication to different areas of a patient's body, or which can be used to simultaneously infuse medication and withdraw blood.

Another object of the present invention is to provide a multiple lumen implantable vascular access port having a configuration which permits each of the lumens to be identified by feeling the patient's skin above the implantation.

A further object of the present invention is to provide a multiple lumen implantable vascular access port which can provide different doses of medication from each of the lumens.

Yet another object of the present invention is to provide a multiple lumen implantable vascular access port in which the various tubes internally associated therewith are reinforced against the type of puncture which would cause leakage. Other objects and attendant advantages of the present invention will readily be perceived hereafter.

The present invention relates to a multiple lumen implantable vascular access port comprising a base, a plurality of separate lumens in said base, a multiple catheter having a plurality of conduits therein with each of said conduits leading to a separate lumen, a tube in communication with each of said lumens, and a nipple received in the adjacent ends of each of said conduits and each of said tubes for effecting communication therebetween.

The present invention also relates to a multiple lumen implantable vascular access port comprising a base, a plurality of separate lumens in said base, a multiple catheter having a plurality of conduits therein, an inner end of each of said plurality of conduits in communication with one of said lumens, and outer ends on said plurality of conduits axially spaced from each other to terminate in spaced portions of a patient's body.

The present invention also relates to a multiple lumen implantable vascular access port comprising a base, a plurality of separate lumens in said base with a base portion between each of said lumens, a plurality of catheter means each having first and second ends with each of said first ends in communication with one of said lumens and each of said second ends remote from each of said lumens, a portion of one of said catheters passing alongside one of said lumens with which it does not communicate and through said base portion, an annular metal cap forming an upper portion of said one of said lumens, a metal base underlying said metal cap and in fluid tight communication therewith, and an overhanging shoulder on said metal cap defining a groove with said metal base, said portion of said one of said catheters being received within said groove to thereby protect said portion of said one of said catheters against inadvertent puncture by a needle passing alongside the outer surface of said cap.

The present invention also relates to a multiple lumen implantable vascular access port comprising a base, a plurality of lumens in said base, catheter means in communication with each of said lumens, and boss means in contiguous relationship to certain of said lumens for identification purposes by feel.

The various aspects of the present invention will be more fully understood when the following portions of the specification are read in conjunction with the accompanying drawings wherein:

BRIEF DESCRIPTION OF THE DRAWINGS

FIG. 1 is a fragmentary perspective view of a multiple lumen implantable vascular port of the present invention containing two lumens;

FIG. 2 is a fragmentary side elevational view of the device of FIG. 1;

FIG. 3 is a cross sectional view taken substantially along line 3—3 of FIG. 1 and showing the construction of one of the lumens and also showing the manner in which this lumen shields a catheter which is connected to another lumen;

FIG. 4 is a fragmentary cross sectional view taken substantially along line 4—4 of FIG. 1;

FIG. 5 is a fragmentary cross sectional view taken substantially along line 5—5 of FIG. 2;

FIG. 6 is a fragmentary enlarged cross sectional view taken substantially along line 6—6 of FIG. 4 and showing the connections between the a multiple catheter and the tubes leading to the lumens;

FIG. 7 is a fragmentary cross sectional view taken substantially along line 7—7 of FIG. 5;

FIG. 8 is a cross sectional view taken along line 8—8 of FIG. 5 and showing particularly the two different sizes of the conduits within the multiple catheter;

FIG. 9 is a fragmentary cross sectional view taken substantially along line 9—9 of FIG. 4 and showing the metal tube inserted in the portion of the tube leading to one of the lumens and located in the central body portion between the two lumens;

FIG. 10 is a fragmentary cross sectional view taken substantially along line 10—10 of FIG. 5; and FIG. 11 is a fragmentary cross sectional view taken substantially along line 11—11 of FIG. 5.

DESCRIPTION OF THE PREFERRED EMBODIMENTS

The present invention relate to a multiple lumen vascular access port which contains two or more lumens. However for simplicity, the following description will refer to a double lumen vascular access port, and it will be appreciated that the constructional details are equally applicable to multiple lumen vascular access ports containing three or more lumens.

The double lumen vascular access port 10 includes an anchoring base 11 of flexible medical grade material, such as silicone rubber, into which lumens 12 and 13 are installed. A plurality of lumens 12 and 13 are identical and therefore only the structure of lumen 12 will be described. Lumen 12 (FIG. 3) includes an annular stainless steel base 14 onto which an annular stainless steel cap 15 is screwed at threaded connection 17. A metal plug 19 is screwed into base 14 at threaded connection 20. A medical grade material 21, such as silicone, may be applied in a circular configuration into a depression in base 19 to function as a stop for a needle or cannula which punctures septum 22 to inject or withdraw fluid from cavity 23. Septum 22 includes an annular peripheral portion 24 which is pressed between shoulder 25 of cap 15 and shoulder 27 of base 14. The foregoing structure of each of lumens 12 and 13 is conventional, and does not form any part of the present invention. Webbing 29, such as DACRON TM, is molded within anchoring base 11, as shown, for reinforcement.

In accordance with the present invention, the multiple catheter 30 is essentially a double conduit which is shown divided into a large conduit 31 and a small conduit 32 by means of a longitudinally extending partition 33 (FIG. 8). Catheter 30 enters anchoring base 11 through integrally molded boss 34 thereof. It will be appreciated that when the vascular access port contains more than two lumens, the multiple catheter can contain an equivalent number of conduits. Boss 34 is built up relatively high so that its uppermost surface 35 is relatively close to the top surface of cap 15 (FIGS. 2 and 4). Thus, when the double lumen vascular access port 10 is implanted under the skin, access port 12 may be identified by feeling boss 34 which is adjacent thereto. When the vascular access port contains a third lumen, a boss similar to boss 34, but smaller, can be used to identify it, or the boss can be oriented relative to boss 34 at a predetermined angle to clearly identify the third lumen. This teaching can be carried to additional lumens.

Catheter 30 is received in opening 37 (FIGS. 4 and 5) in boss 34. A metal nipple or tube 39 is received in the end 40 of large conduit 31 and is also received in tube 41 which leads to chamber 23 and is in fluid-tight contact with bore 42 of base 14. The metal tube 39 prevents a needle which may slide down the outside frustoconical surface 43 of cap 15 from perforating tube 41 in such a manner so as to cause it to leak. The end 44 of metal tube 39 terminates under ledge 45 (FIG. 11) of cap 15, thereby further assuring that a needle sliding downwardly on frustoconical surface 43 cannot puncture tube 41 so as to cause leakage.

A metal nipple or tube 47 (FIG. 6) is also inserted into small conduit 32 and into the end 49 of a tube 50 which terminates at chamber 23' of port 13 and has its end 51 sealed in fluid-tight engagement with base 14' of lumen 13. Metal tube 47 has an end 53 which also underlies shelf 45 to prevent leakable puncture of tube 50 by a needle sliding down frustoconical surface 43. The central portion 54 of tube 50 lies under shelf 45 of cap 15 as shown in FIG. 3, and therefore a needle sliding down frustoconical surface 43 will miss tube portion 50. If the multiple access port contains three lumens, a conduit portion which is analogous to conduit portion 54 and leading to the third lumen can be located in the groove on the opposite side of lumen 12 from a conduit portion 54.

A metal tube 55 (FIGS. 5, 9 and 10) is located within tube 50 and its end 57 lies under the shelf 45' of lumen 13, which is analogous to shelf 45 of lumen 12, so that a needle sliding down frustoconical surface 43' will not be able to puncture tube 50 to an extent which will cause leakage. In a vascular access port containing a third lumen, a metal tube analogous to tube 55 is associated with the third lumen for the same purpose.

It can thus be seen that the improved double lumen vascular access port of the present invention is manifestly capable of achieving the above enumerated objects, and while preferred embodiments of the present invention have been disclosed, it will be appreciated that it is not limited thereto but may be otherwise embodied within the scope of the following claims.

What is claimed is:

1. A double lumen implantable vascular access port comprising a base, first and second separate lumens in said base, a double catheter having first and second conduits therein, a first tube in communication with said first lumen, a second tube in communication with said second lumen, a first nipple received in the adjacent ends of said first conduit and said first tube for effecting communication therebetween, a second nipple received in the adjacent ends of said second conduit and a second tube for effecting communication therebetween, a central base portion between said first and second lumens, said second conduit including a central conduit portion passing through said central base portion, and tube means in said central conduit portion for reinforcing said central conduit portion against puncture.

2. A double lumen implantable vascular access port as set forth in claim 1 wherein said first and second nipples are metal tubes.

3. A double lumen implantable vascular access port as set forth in claim 1 wherein said double catheter includes first and second outer end portions remote from said base, said first outer end portion comprising the terminal of said first conduit, and said second outer end portion comprising the outer end portion of said second conduit, said first and second outer end portions being axially spaced from each other to terminate in spaced portions of a patient's body.

4. A double lumen implantable vascular access port as set forth in claim 1 wherein said first and second conduits are of different effective cross sectional area.

5. A double lumen implantable vascular access port as set forth in claim 1 wherein said first and second lumens include first and second caps, respectively, first and second outer surfaces on said first and second caps, respectively, first and second overhanging shoulders on said first and second caps, respectively, and first and second end portions on said first and second nipples, respectively, said first and second end portions being the portions of said first and second nipples, respectively, which are received in said first and second tubes, respectively, said first and second end portions of said first and second nipples, respectively, being located under said first and second overhanging shoulders, respectively, to reinforce said first and second tubes against inadvertent puncture by a needle passing alongside said first and second outer surfaces, respectively, of said first and second caps, respectively.

6. A double lumen implantable vascular access port as set forth in claim 1 wherein said tube means comprises a portion of said second nipple.

7. A double lumen implantable vascular access port as set forth in claim 1 including base means in contiguous relationship to said first lumen for identifying it by feel.

8. A multiple lumen implantable vascular access port comprising a base, a plurality of separate lumens in said base, a multiple catheter having a plurality of conduits therein with each of said conduits leading to a separate lumen, a tube in communication with each of said lumens, a nipple received in the adjacent ends of each of said conduits and each of said tube for effecting communication therebetween, and a central base portions between said plurality of lumens, certain of said conduits including a central conduit portion passing through said central base portion, and a metal tube in certain of said central conduit portions for reinforcing certain of said central conduit portions against puncture.

9. A multiple lumen implantable vascular access port as set forth in claim 8 wherein certain of said lumens include caps, outer surfaces on said caps, overhanging shoulders on said caps, and end portions on said nipples received in said tubes and located under said overhanging shoulders to reinforce said tubes against inadvertent puncture by needles passing alongside said outer surfaces.

10. A multiple lumen implantable vascular access port as set forth in claim 8 wherein said nipples are metal tubes.

11. A multiple lumen implantable vascular access port as set forth in claim 8 wherein said multiple catheter includes outer end portions remote from said base, said outer end portions comprising the terminals of said conduits which are axially spaced from each other so as to terminate in spaced portions of a patient's body.

12. A multiple lumen implantable vascular access port comprising a base, a plurality of separate lumens in said base with a base portion between each of said lumens, a plurality of catheter means each having first and second ends with each of said first ends in communication with an associated lumen and each of said second ends remote from its associated lumen, a portion of one of said catheters passing alongside one of said lumens with which it does not communicate and through said base portion, an annular metal cap forming an upper portion of said one of said lumens, an outer surface on said cap, a metal base underlying said metal cap and in fluid tight communication therewith, and an overhanging shoulder on said metal cap defining a groove with said metal base, said portion of said one of said catheters being received within said groove to thereby protect said portion of said one of said catheters against inadvertent puncture by a needle passing alongside said outer surface of said cap.

13. A double lumen implantable vascular access port comprising a base, first and second separate lumens in said base with a base portion therebetween, first catheter means having first and second ends with said first end in communication with said first lumen and said second end remote from said first lumen, second catheter means having a first end in communication with said second lumen and a second end remote from said second lumen, a portion of said second catheter passing alongside said first lumen and through said base portion to said second lumen, a cap forming an upper portion of said first lumen, and an outer portion on said cap, said portion of said second catheter being located under said outer portion of said cap to thereby protect said portion of said second catheter against inadvertent puncture by a needle passing alongside said outer portion of said cap.

14. A multiple lumen implantable vascular access port comprising a base, a plurality of separate lumens in said base with a base portion between each of said lumens, a plurality of catheter means each having first and second ends with each of said first ends in communication with an associated lumen and each of said second ends remote from its associated lumen, a portion of one of said catheters passing alongside one of said lumens with which it does not communicate and through said base portions, a cap forming an upper portion of said one of said lumens, and an outer portion on said cap, said portion of said one of said catheters being located under said outer portion of said cap to thereby protect said portion of said one of said catheters against inadvertent puncture by a needle passing alongside said outer portion of said cap.

15. A multiple lumen vascular access port comprising a base, first and second lumens in said base, a central base portion between said first and second lumens, first and second catheters, first and second tubes in communication with said first and second lumens, respectively, said first and second catheters each having first and second ends, first and second nipples in said first and second tubes, respectively, said first nipple also being in said first end of said first catheter and said second nipple also being in said first end of said second catheter, first and second caps on said first and second lumens respectively, first and second overhanging shoulders on said first and second caps, respectively, first and second outer surfaces on said first and second caps, respectively, said first and second nipples including portions located under said first and second shoulders to reinforce said first and second tubes against puncture by needles passing alongside said outer surfaces of said caps, said second nipple also passing through said central base portion and terminating under said first shoulder to reinforce said second catheter against puncture by a needle passing along the outside of said first cap.

16. A multiple lumen vascular access port comprising a base, first and second lumens in said base, a central base portion between said first and second lumens, first and second catheters, a tube in communication with said first lumen, said first and second catheters each having first and second ends, said first end of said second catheter being in communication with said second lumen, said second ends of said first and second catheters being remote from said first and second lumens, respectively, a nipple in said first tube, said nipple also being in said first end of said first catheter, first and second caps on said first and second lumens, respectively, first and second overhanging shoulders on said first and second caps, respectively, first and second outer surfaces on said first and second caps, respectively, said nipple including portions located under said first and second shoulders and a portion passing through said central base portion to reinforce said first tube and said first end of said first catheter against puncture by needles passing alongside said outer surfaces of said first and second caps and through said central base portion.

17. A double lumen implantable vascular access port comprising a base, first and second separate lumens in said base with a base portion therebetween, first catheter means having first and second ends with said first end in communication with said first lumen and said second end remote from said first lumen, second catheter means having a first end in communication with said second lumen and a second end remote from said second lumen, a portion of said second catheter passing alongside said first lumen and through said base portion to said second lumen, an annular metal cap forming an upper portion of said first lumen, an outer surface on said cap, a metal base underlying said metal cap and in fluid tight communication therewith, and an overhanging shoulder on said metal cap defining a groove with said metal base, said portion of said second catheter being received within said groove to thereby protect said portion of said second catheter against inadvertent puncture by a needle passing alongside said outer surface of said cap.

* * * * *